US010159254B2

(12) United States Patent
Jain et al.

(10) Patent No.: US 10,159,254 B2
(45) Date of Patent: Dec. 25, 2018

(54) WEED CONTROL METHODS

(71) Applicant: Syngenta Participations AG, Basel (CH)

(72) Inventors: Rakesh Jain, Vero Beach, FL (US); Brett Robert Miller, Minnetonka, MN (US); Gordan Dean Vail, Greensboro, NC (US); Bryan James Ulmer, Basel (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/779,200

(22) PCT Filed: Mar. 21, 2014

(86) PCT No.: PCT/EP2014/055705
§ 371 (c)(1),
(2) Date: Sep. 22, 2015

(87) PCT Pub. No.: WO2014/154583
PCT Pub. Date: Oct. 2, 2014

(65) Prior Publication Data
US 2016/0058014 A1 Mar. 3, 2016

Related U.S. Application Data

(60) Provisional application No. 61/804,917, filed on Mar. 25, 2013.

(51) Int. Cl.
| | | |
|---|---|---|
| *A01N 59/16* | (2006.01) | |
| *A01N 41/10* | (2006.01) | |
| *A01N 43/40* | (2006.01) | |
| *A01N 55/02* | (2006.01) | |
| *A01N 43/56* | (2006.01) | |
| *A01N 43/80* | (2006.01) | |

(52) U.S. Cl.
CPC ............ *A01N 59/16* (2013.01); *A01N 41/10* (2013.01); *A01N 43/40* (2013.01); *A01N 43/56* (2013.01); *A01N 43/80* (2013.01)

(58) Field of Classification Search
CPC ........ A01N 59/16; A01N 41/10; A01N 43/56; A01N 55/02
See application file for complete search history.

(56) References Cited

U.S. PATENT DOCUMENTS

| | | | | |
|---|---|---|---|---|
| 5,912,207 A | * | 6/1999 | Scher | A01N 35/06 504/190 |
| 6,271,177 B1 | * | 8/2001 | Hudetz | A01N 25/32 504/124 |
| 2002/0016491 A1 | | 2/2002 | Scher et al. | |
| 2006/0084575 A1 | * | 4/2006 | Sedun | A01N 37/32 504/166 |
| 2007/0197386 A1 | | 8/2007 | Diebold et al. | |
| 2009/0172831 A1 | * | 7/2009 | Andrews | C12N 9/0069 800/278 |
| 2011/0269626 A1 | * | 11/2011 | James | A01N 41/10 504/112 |
| 2013/0097726 A1 | * | 4/2013 | Ader | C12N 15/8243 800/278 |

FOREIGN PATENT DOCUMENTS

| | | |
|---|---|---|
| WO | 9702747 A1 | 1/1997 |
| WO | 97027748 A1 | 8/1997 |
| WO | 02046387 A2 | 6/2002 |
| WO | 03073856 A1 | 9/2003 |

OTHER PUBLICATIONS

BASF prduct sheet on Sequestrene 138 Fe(TM), obtained on line Sep. 2017.*
WPI World Patent Information Derwent, vol. 39 No. 79, 1979, XP002018980.
International Search Report of International application PCT/EP2014/055705 dated May 27, 2014.

* cited by examiner

*Primary Examiner* — Mina Haghighatian
(74) *Attorney, Agent, or Firm* — Dinsmore & Shohl LLP; Toni-Junell Herbert

(57) ABSTRACT

The present invention relates, inter alia, to a method of improving the tolerance of a plant, which has been genetically engineered to over express a p-hydroxyphenylpyruvate dioxygenase (HPPD), to a HPPD inhibiting herbicide, said method comprising applying to said plant a water-soluble iron-containing compound. The present invention further relates to a method of selectively controlling weeds at a locus, the locus comprising weeds and crop plants, the crop plants having been genetically engineered to overexpress a HPPD which confers tolerance to a HPPD-inhibiting herbicide, the method comprising application to the locus of (i) a weed controlling amount of a HPPD-inhibiting herbicide and (ii) a water-soluble iron-containing compound. The present invention further relates to herbicidal compositions comprising a HPPD-inhibiting herbicide and a water-soluble iron-containing compound.

8 Claims, No Drawings

WEED CONTROL METHODS

RELATED APPLICATION INFORMATION

This application is a 371 of International Application No. PCT/EP2014/055705, filed 21 Mar. 2014, which claims priority to 61/804,917, filed 25 Mar., 2013, the contents of which are incorporated herein by reference herein.

The present invention relates, inter alia, to improved weed control methods which employ p-hydroxyphenylpyruvate dioxygenase (HPPD) inhibiting herbicides. Plants that have been genetically engineered to be tolerant to HPPD-inhibiting herbicides are known, for example, from WO02/46387, WO2012/082542 and WO2012/082548. In these cases, the tolerance is achieved by over-expression of HPPD. Whilst the tolerance observed in respect of the engineered plants is often very good, there exists an opportunity to improve the tolerance further, in order to improve crop safety and enable the commercial use of a broader range of HPPD inhibitors in conjunction with the engineered plants across extended use patterns relative to the innate tolerance expressed by these engineered plants. It has surprisingly been found that the tolerance of such engineered plants can be improved (safened) significantly by applying to the engineered plants a water-soluble iron-containing compound.

Thus, according to the present invention there is provided a method of improving the tolerance of a plant, which has been genetically engineered to over-express a HPPD, to a HPPD inhibiting herbicide, said method comprising applying to said plant a water-soluble iron-containing compound.

Several examples of plants which are tolerant to HPPD-inhibiting herbicides, achieved via over-expression of HPPD, are known for example as disclosed in WO02/46387. Suitable HPPDs can thus be derived from bacteria, more particularly from *Pseudomonas fluorescens* or *Shewanella colwelliana*, or from a plant, more particularly, derived from a monocot plant or, yet more particularly, from a barley, maize, wheat, rice, *Brachiaria, Chenchrus, Lolium, Festuca, Setaria, Eleusine, Sorghum* or *Avena* species. The HPPD may also have been mutated to increase the tolerance of the enzyme to HPPD-inhibiting herbicides. The plants which are tolerant to HPPD-inhibiting herbicides via over-expression of HPPD will typically be crop plants, such as cereals, for example barley and wheat, cotton, oilseed rape, sunflower, maize, rice, soybeans, sugar beet and sugar cane. In a preferred aspect of the present invention, the plant is soybean. Several HPPD-tolerant soybean transgenic "events" are known, and include for example SYHT04R (WO2012/082542), SYHT0H2 (WO2012/082548) and FG72.

The crop plants may also have been rendered tolerant to other herbicides or classes of herbicides (e.g. ALS-, GS-, EPSPS-, PPO-Auxins, and ACCase-inhibitors) by conventional methods of breeding or by genetic engineering. Examples of crops that have been rendered tolerant to herbicides by genetic engineering methods include e.g. glyphosate, glufosinate, isoxaflutole, dicamba, imidazolinone and 2,4-D resistant soybean varieties commercially or soon to be commercially available under the trade names RoundupReady®, LibertyLink®, BalanceGT®, RoundupReady® Xtend, Cultivance® and Enlist® respectively.

Thus, in another aspect of the present invention there is provided a method of selectively controlling weeds at a locus (typically a field), the locus comprising weeds and crop plants, the crop plants having been genetically engineered to overexpress a HPPD which confers tolerance to a HPPD-inhibiting herbicide, the method comprising application to the locus of (i) a weed controlling amount of a HPPD-inhibiting herbicide and (ii) a water-soluble iron-containing compound. One surprising aspect of the present invention is that it appears that the safening observed upon application of the water-soluble iron-containing compound to the locus is specific for the plant which has been genetically engineered to overexpress a HPPD. No significant safening is observed in respect of the weed species being controlled.

It should be understood that, if desired, the water-soluble iron-containing compound can be applied to the locus before application of the HPPD-inhibiting herbicide is made. For example, the water-soluble iron-containing compound can be applied to the locus up to seven days before the HPPD-inhibiting herbicide is applied. It may be applied as a broadcast foliar application but is also possible to apply the iron-containing compound as a seed treatment/dressing to the crop plant.

In a preferred aspect of the invention, the water-soluble iron-containing compound is applied to the locus comprising the crop plant simultaneously with the HPPD-inhibiting herbicide. Typically, this will be achieved by tank-mixing a herbicidal composition comprising the HPPD-inhibiting herbicide with the water-soluble iron-containing compound. It is also possible that the HPPD-inhibiting herbicide be provided as a "pre-mix" herbicidal composition which also includes the iron-containing compound and which is simply diluted appropriately in the spray tank. Thus, according to the present invention there is also provided a herbicidal composition, including a pre-mix (concentrate) composition, comprising a HPPD-inhibiting herbicide and a water-soluble iron-containing compound. The herbicidal composition, diluted where necessary, is typically applied to the relevant locus by spraying, for example via a tractor mounted sprayer for large areas, but other methods such as dusting (for powders), drip or drench can also be used. The application may be made to the locus pre-emergence or post-emergence of the plant which has been genetically engineered to over-express a HPPD.

Suitable water-soluble iron-containing compounds include, for example, ionic iron salts and iron chelates, wherein the iron may have the oxidation number of +2 or +3. Suitable iron salts include, for example, iron (II) sulphate (ferrous sulphate) and ferric ammonium citrate. Iron chelates are particularly preferred in the context of the present invention, especially those formed with e.g ethylenediamine tetraacetic acid (EDTA): 2-[2-[[2-Hydroxy-1-(2-hydroxyphenyl)-2-oxoethyl]amino]ethylamino]-2-(2-hydroxyphenyl)acetic acid (EDDHA); ethylenediamine-di (o-hydroxy-o-methylphenylacetic) acid (EDDHMA); ethylenediamine-N,N'-bis(2-hydroxy-5-sulfonylphenyl) (EDDHSA); ethylenediamine-di-(2-hydroxy-4-carboxyphenylacetic) acid (EDDCHA) and diethylenetriaminepentacetic acid (DTPA). Iron chelates may be a mixture of isomers, for example EDDHA is a mixture of iron (III) complexes of the two diasteroisomers of ethylene-N,N'-di(2-hydro-phenyl acetate) and iron (III) complexes of the two diasteroisomers of ethylenediamine-N-(2-hydroxyphenylacetate)-N'-(4-hydroxyphenyl acetate). Depending on the pH of the composition, the iron chelate may be present in the form of a salt, for example an alkali metal salt such as a sodium salt. The preparation of such iron chelates and there use as micronutrients in agriculture is known, for example, from U.S. Pat. No. 2,921,847. Several commercial forms of the above-mentioned iron chelates are known in the art. For example, an iron DTPA mixture is available as Sequestrene® 330. In a preferred aspect of the invention, the water soluble iron-containing compound is selected from the group consisting of iron DTPA (Sequestrene® 330), EDDHA-FeNa (Sequestrene® 138) and ferrous sulfate. In the context of the present invention, use of EDDHA-FeNa (a ferric sodium complex of EDDHA), commercially available as Sequestrene® 138Fe, which contains 6% iron in the form of EDDHA (ethylenediamine-N—N'-bis (2 hydroxyphenylacetic acid) chelated product), is particularly preferred. EDDHA chelated iron is also commercially available as Soygreen®. The iron can typically be applied to the locus at an equivalent rate of from 1 g to 1000 g/ha, more typically from 6 g to 240 g/ha. Thus, in the context of iron chelate such as Sequestrene® 138Fe, the actual product is typically applied at a rate of from 100 g to 4000 g/ha, more preferably from 200 to 2000 g/ha.

Herbicides that act by inhibiting HPPD are well known in the art. Inhibition of HPPD blocks the biosynthesis of plastoquinone (PQ) from tyrosine. PQ is an essential cofactor in the biosynthesis of carotenoid pigments which are essential for photoprotection of the photosynthetic centres. HPPD-inhibiting herbicides are phloem-mobile bleachers which cause the light-exposed new meristems and leaves to emerge white where, in the absence of carotenoids, chlorophyll is photo-destroyed and becomes itself an agent of photo-destruction via the photo-generation of singlet oxygen.

The safening effect conferred by the iron-containing compound has been observed in respect of a broad range of chemically diverse HPPD-inhibiting herbicides, indicating that the iron-containing compounds have broad utility with regard to safening HPPD-inhibiting herbicides in plants. HPPD-inhibiting herbicides include, for example, benzobicyclon (CAS RN 156963-66-5), mesotrione (CAS RN 104206-82-8), sulcotrione (CAS RN 99105-77-8), tefuryltrione (CAS RN 473278-76-1), tembotrione (CAS RN 335104-84-2), fenquinotrione (1342891-70-6), bicyclopyrone (CAS RN 352010-68-5), ketospiradox (CAS RN 192708-91-1) or its free acid (CAS RN 187270-87-7), benzofenap (CAS RN 82692-44-2), pyrasulfotole (CAS RN 365400-11-9), pyrazolynate (CAS RN 58011-68-0), pyrazoxyfen (CAS RN 71561-11-0), topramezone (CAS RN 210631-68-8), isoxachlortole (CAS RN 141112-06-3) and isoxaflutole (CAS RN 141112-29-0). More recent examples of HPPD-inhibiting herbicides which can also be used in the context of the present invention are reported in WO2009/016841, WO2009/115788, WO2010/089993, WO2010/116122, WO2011/031658, WO2011/035874, WO2012/002096, WO2012/033548, WO2012/028579 and WO2012136703.

Preferably, the HPPD-inhibiting herbicide is selected from the group consisting of mesotrione, sulcotrione, tembotrione, bicyclopyrone, pyrasulfotole, topramezone and isoxaflutole, more preferably selected from the group consisting of mesotrione, bicyclopyrone, tembotrione and isoxaflutole.

The rate of application of the HPPD-inhibiting herbicide may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The herbicide is typically applied at a rate of from 10 to 2000 g active ingredient/ha, especially from 50 to 1000 g active ingredient/ha and more typically from 50 to 500 g active ingredient/ha.

In a preferred aspect of the present invention, the herbicidal composition of the present invention referred to above comprises a HPPD-inhibiting herbicide as defined above. In a more preferred aspect, the HPPD-inhibitor is selected from the group consisting of mesotrione, sulcotrione, tembotrione, bicyclopyrone, pyrasulfotole, topramezone and isoxaflutole, more preferably selected from the group consisting of mesotrione, bicyclopyrone, tembotrione and isoxaflutole. The actual concentration of the HPPD-inhibitor within the herbicide composition will vary, for example depending on the exact nature of the HPPD-inhibitor, and the exact composition type. In the context of a pre-mix (concentrate) composition, the HPPD-inhibitor will typically be present from 0.5% w/w to 50% w/w, more typically from 5% to 50% w/w and even more typically from 10 to 40% w/w.

In another preferred aspect of the present invention, the herbicidal composition of the present invention referred to above comprises a water-soluble iron-containing compound as defined above. In a more preferred embodiment, the water-soluble iron-containing compound in the herbicidal composition is selected from the group consisting of iron DTPA (Sequestrene® 330), EDDHA-FeNa (Sequestrene® 138) and ferrous sulfate. The actual concentration of the water-soluble iron-containing compound within the herbicide composition will vary, for example depending on the exact nature of the water-soluble iron-containing compound, and the exact composition type. In the context of a pre-mix (concentrate) composition, the water-soluble iron-containing compound will typically be present at an amount which provides from 1% to 10% w/w iron in the form of the chelate or the ionic salt.

The herbicidal composition of the present invention may also comprise further conventional agrochemical adjuvants such as wetters, dispersants, surface-active agents and other activity enhancers. The herbicidal composition may further comprise further herbicidal components that are appropriate for the crop to which the herbicidal composition is applied. Thus, with regard to soybean the herbicidal composition may further comprise, for example, glyphosate, glufosinate and fomesafen or agrochemically acceptable salts thereof. In some crop applications, the addition of a herbicide safener may also be beneficial.

The pre-mix (concentrate) herbicidal composition of the present invention may be provided in a wide variety of formulation types, for example a liquid formulation (e.g an aqueous formulation type such as a suspension concentrate (SC)), or in a solid formulation such as a wettable powder (WP) or granule (WG). If a granule is employed, this can be directly applied to the locus or diluted in a spray tank.

EXAMPLES

Example 1

Effect of Tank-mix and Sequential Application of Sequestrene® 138 on Mesotrione (Applied as Callisto®)—Maximum Injury in SYHT0H2 Soybeans An experiment is conducted in the greenhouse to determine the effect of chelated iron (Sequestrene 138Fe containing 6% iron) on HPPD-inhibitor injury to SYHT0H2 soybeans. Soybeans are grown in pots filled with a greenhouse potting mix. When the plants reach the V2-V3 stage, they are sprayed with an HPPD-inhibitor herbicide applied alone (Treatment 1), or in tank mixture with Sequestrene 138Fe (Treatment 2), or sequentially with Sequestrene 138Fe applied 1 day before the HPPD inhibitor (Treatment 3). Sequestrene 138Fe is applied at 2240 g/ha (equivalent to 134 g iron/ha). All treatments are applied with liquid ammonium sulfate @ 2.5% v/v and a non-ionic surfactant (NIS) @ 0.25% v/v in 150 L/ha water. Observations on percent injury are recorded 5, 11, or 22 days after treatment. Data presented are maximum injury observed during the trial.

| Treatment | Mesotrione Rate g ai/ha | Sequestrene® 138Fe g/ha | % Maximum Injury |
|---|---|---|---|
| 1 | 420 | — | 20 |
| 2 (simultaneous) | 420 | 2240 | 0 |
| 3 (sequential) | 420 | 2240 | 7 |

| Treatment | Bicyclopyrone Rate g ai/ha | Sequestrene® 138Fe g/ha | % Maximum Injury |
|---|---|---|---|
| 1 | 200 | — | 25 |
| 2 (simultaneous) | 200 | 2240 | 3 |
| 3 (sequential) | 200 | 2240 | 12 |

| Treatment | Tembotrione Rate g ai/ha | Sequestrene® 138Fe g/ha | % Maximum Injury |
|---|---|---|---|
| 1 | 368 | — | 31 |
| 2 (simultaneous) | 368 | 2240 | 3 |
| 3 (sequential) | 368 | 2240 | 17 |

These data show that Sequestrene 138Fe is very effective in reducing HPPD-inhibitor injury on SYHT0H2 soybeans when it is applied in combination with the HPPD-inhibitor or as a sequential application 1 day before the HPPD inhibitor application.

Example 2

Effect of Sequestrene® 138Fe on Percent Injury from Various HPPD-inhibitors on SYHT0H2 Soybeans. Injury Assessed at Seven Days after Treatment (7 DAT)

SYHT0H2 soybeans are grown in 4×4-inch pots filled with a greenhouse potting mix. When the plants reach the V2-V3 growth stage, they are treated with an HPPD inhibitor applied alone or in a tank mixture with Sequestrene 138Fe at various rates ranging from 140 g product/ha (equivalent to 8.4 g iron/ha) to 2240 g product/ha (equivalent to 134 g iron/ha). All treatments are applied with liquid ammonium sulfate at 2.5% v/v and NIS at 0.25% v/v in 150 L/ha water.

| Herbicide | Rate g/ha | Sequestrene® 138Fe g/ha | % Injury |
|---|---|---|---|
| Mesotrione | 420 | 0 | 15 |
|  |  | 140 | 13 |
|  |  | 280 | 2 |
|  |  | 560 | 1 |
|  |  | 1120 | 0 |
|  |  | 2240 | 0 |
| Bicyclopyrone | 200 | 0 | 23 |
|  |  | 140 | 12 |
|  |  | 280 | 10 |
|  |  | 560 | 1 |
|  |  | 1120 | 0 |
|  |  | 2240 | 0 |
| Tembotrione | 368 | 0 | 22 |
|  |  | 140 | 18 |
|  |  | 280 | 5 |
|  |  | 560 | 0 |
|  |  | 1120 | 0 |
|  |  | 2240 | 0 |
| Topramezone | 72 | 0 | 8 |
|  |  | 140 | 0 |
|  |  | 280 | 0 |
|  |  | 560 | 0 |
|  |  | 1120 | 0 |
|  |  | 2240 | 0 |

These results show that Sequestrene 138Fe is highly effective in eliminating the injury on SYHT0H2 soybeans from mesotrione at rates as low as 280 g/ha. A slightly higher rate, i.e. 560 g/ha, was required to completely safen the soybeans from bicyclopyrone or tembotrione injury.

Example 3

Effect of Tank Mix Applications of HPPD Inhibitors and Sequestrene® 138Fe on Velvetleaf Control. Percent Control Assessed 19 DAT A greenhouse experiment is conducted to determine the effect of chelated iron on weed control in the greenhouse. Velvetleaf (*Abutilon theophrasti*) and common waterhemp (*Amaranthus rudis*) plants are grown in 4×4-inch pots filled with a greenhouse potting mix. When the plants reached the 2 to 3 inch height (2 to 3 leaf stage), they are sprayed with a reduced rate of an HPPD inhibitor alone or in a tank mix combination with Sequestrene 138Fe at 140 g/ha (equivalent to 8.4 g iron/hectare) or 280 g/ha (equivalent to 16.8 g iron/hectare). All treatments are applied with liquid ammonium sulfate at 2.5% v/v and NIS at 0.25% v/v in 150 L/ha water. Observations on percent control are recorded 12, 19, and 25 days after treatment.

| Treatment | HPPD Inhibitor | Rate g ai/ha | Sequestrene® 138Fe g/ha | % Injury |
|---|---|---|---|---|
| 1 | Mesotrione | 26 | 0 | 100 |
| 2 |  | 26 | 140 | 100 |
| 3 | Isoxaflutole | 26 | 0 | 78 |
| 4 |  | 26 | 140 | 82 |
| 5 | Bicyclopyrone | 50 | 0 | 100 |
| 6 |  | 50 | 280 | 100 |
| 7 | Tembotrione | 46 | 0 | 98 |
| 8 |  | 46 | 280 | 99 |
| 9 | Pyrasulfatole | 22 | 0 | 85 |
| 10 |  | 22 | 280 | 80 |
| 11 | Topramezone | 18 | 0 | 96 |
| 12 |  | 18 | 280 | 93 |

These results show that Sequestrene 138Fe has a minimal effect on velvetleaf control with various HPPD-inhibiting herbicides when they are applied with chelated iron.

Experiment 4

Effect of Tank Mix Applications of Various HPPD Inhibitors and Sequestrene 138Fe on Common Waterhemp Control. Injury Assessed 17 DAT An experiment is performed to look at the effect of applying iron chelates on control of Common Waterhemp using HPPD-inhibiting herbicides. Experiment design is analogous to that outlined in Experiment 3 above.

| Treatment | HPPD Inhibitor | Rate g ai/ha | Sequestrene ® 138Fe g/ha | % Injury |
|---|---|---|---|---|
| 1 | Mesotrione | 26 | 0 | 77 |
| 2 | | 26 | 140 | 78 |
| 3 | Isoxaflutole | 26 | 0 | 87 |
| 4 | | 26 | 140 | 88 |
| 5 | Bicyclopyrone | 50 | 0 | 90 |
| 6 | | 50 | 280 | 96 |
| 7 | Tembotrione | 46 | 0 | 99 |
| 8 | | 46 | 280 | 99 |
| 9 | Pyrasulfatole | 22 | 0 | 98 |
| 10 | | 22 | 280 | 77 |
| 11 | Topramezone | 18 | 0 | 100 |
| 12 | | 18 | 280 | 99 |

Similar to the results on velvetleaf, Sequestrene 138Fe applied had minimal effect on common waterhemp control with any of the HPPD inhibitors, with the exception of a slight reduction in control seen when Sequestrene 138Fe was applied with pyrasulfatole.

Example 5

Effect of Sequestrene® 138Fe on Various
HPPD-inhibitors in SYHT04R Soybeans.
Maximum Injury Assessed 6 Days after Treatment A greenhouse experiment is conducted to determine if Sequestrene® 138Fe was effective in safening various other HPPD herbicide-tolerant soybean events, such as SYHT04R.

SYHT04R soybean plants are grown in 4×4-inch pots filled with a greenhouse potting mix. When the plants reached the V2-V3 growth stage, they are sprayed with an HPPD inhibitor alone or in combination with Sequestrene® 138Fe at 1120 g/ha (equivalent to 67.2 g iron/ha). All treatments were applied with liquid ammonium sulfate at 2.5% v/v and NIS at 0.25% v/v. Observations on percent injury are recorded at 6 and 20 days after treatment. Data presented is from the 6 days after treatment rating representing the maximum injury observed during the experiment.

| Herbicide | Rate g/ha | Sequestrene ® 138Fe g/ha | % Injury |
|---|---|---|---|
| Mesotrione | 420 | 0 | 23 |
| | | 1120 | 3 |
| Bicyclopyrone | 200 | 0 | 29 |
| | | 1120 | 7 |
| Isoxaflutole | 280 | 0 | 28 |
| | | 1120 | 10 |

Results showed that Sequestrene® 138Fe was highly effective in safening SYHT04R soybeans from post-emergence HPPD inhibitor injury.

Example 6

The Ability of Water-soluble Iron Compounds to
Safen HPPD-inhibitors in SYHT0H2 Soybeans An experiment is conducted to look at the safening effect of a variety of water-soluble iron-containing compounds. SYHT0H2 soybean plants are grown in small pots filled with a greenhouse potting mix. Plants are sprayed with mesotrione alone or in combination with EDTA alone (non-iron containing control) or an iron-containing compound using a laboratory sprayer calibrated to deliver 150 L/ha. In all cases, mesotrione was applied at 420 g ai/ha and all treatments contained liquid ammonium sulphate at 2.5% v/v and NIS at 0.25% v/v. The application rates of iron-containing compounds indicated are iron equivalent rates. For the EDTA (non-Fe) control, the indicated rates are equivalent to those used with regard to the EDTA ferric sodium salt. Percent injury levels were assessed 6, 9, and 16 days after treatment. Data presented are maximum injury occurring from any of the treatments at any time during the experiment.

| Herbicide | Additive | Rate g/ha | % Injury |
|---|---|---|---|
| Mesotrione | None | — | 17 |
| Mesotrione | EDTA (non-Fe control) | 34 | 22 |
| | | 67 | 25 |
| | | 134 | 22 |
| | | 336 | 22 |
| | | 672 | 15 |
| Mesotrione | EDTA-ferric sodium salt | 34 | 18 |
| | | 67 | 3 |
| | | 134 | 10 |
| Mesotrione | Sequestrene 330-Fe | 34 | 12 |
| | | 67 | 13 |
| | | 134 | 5 |
| Mesotrione | Sequestrene 138-Fe | 37 | 0 |
| | | 67 | 3 |
| | | 134 | 0 |
| Mesotrione | Ferrous Sulfate ($Fe_2SO_4$) | 37 | 10 |
| | | 67 | 7 |
| | | 134 | 2 |
| | | 268 | 2 |

The experiment shows that EDTA alone was not effective in safening SYHT0H2 soybeans from mesotrione injury. However, Sequestrene 330Fe (EDTA-Fe), Sequestrene 138Fe and $Fe_2SO_4$ are all effective in safening SYHT0H2 soybeans from mesotrione injury.

Example 7

Effect of Chelated Fe and Chelated Mn on
Safening SYHT04R Soybean from Bicyclopyrone
Injury A greenhouse experiment is conducted to determine if chelating agents containing nutrient elements other than Fe were also effective in safening HPPD herbicide-tolerant soybeans.

SYHT04R soybean plants are grown in 4×4-inch pots filled with a greenhouse potting mix. When the plants reached the V2-V3 growth stage, they are sprayed with an HPPD inhibitor alone or in combination with Sequestrene 138Fe or a solution containing 6% EDTA-chelated Mn. All treatments are applied with liquid ammonium sulfate at 2.5% v/v and NIS at 0.25% v/v. Observations on percent injury were recorded 5, and 9 days after treatment. Data presented are maximum injury observed during the experiment.

| Herbicide | Additive | Rate g/ha | % Injury |
|---|---|---|---|
| Bicyclopyrone | None | — | 29 |
| Bicyclopyrone | Sequestrene 138-Fe | 67 | 2 |

-continued

| Herbicide | Additive | Rate g/ha | % Injury |
|---|---|---|---|
| Bicyclopyrone | EDTA Chelated Mn | 67 | 28 |
| Bicyclopyrone | EDTA Chelated Mn | 134 | 26 |

These results indicate that the safening observed in respect of iron containing chelates is not observed with regard to Mn containing chelates.

Example 8

Safening of Various HPPD-inhibiting Herbicides in HPPD-tolerant Soybean Events SYHT04R and SYHT0H2

An experiment is performed to determine whether the addition of chelating iron to the spray formulation can mitigate foliar bleaching injury from the HPPD herbicides mesotrione, bicyclopyrone, tembotrione, isoxaflutole, topramezone and pyrasulfatole when applied post-emergence to the HPPD-tolerant soybean events SYHT04R and SYHT0H2.

Soybean plants are grown in a glasshouse (24° C. day, 18° C. night; 65% relative humidity; 16 hour photoperiod). Two replicates are utilised in respect of SYHT0H2 (growth stage V1-V3) and three replicates are utilised in respect of SYHT04R (growth stage V1 to V3). Spray applications are applied post-emergence at 200l/ha. Herbicide damage was assessed 7 DAA (Days After Application).

| Treatment number | Compound 1 | Compound 1 g ai/ha | Sequestrene 138Fe g/ha | SYHT0H2 | SYHT04R |
|---|---|---|---|---|---|
| 1 | Mesotrione | 200 | n/a | 13 | 8 |
| 3 |  | 800 |  | 23 | 32 |
| 4 | Mesotrione | 200 | 1000 | 3 | 2 |
| 6 |  | 800 | 1000 | 18 | 17 |
| 7 | Bicyclopyrone | 100 | n/a | 13 | 15 |
| 9 |  | 400 |  | 40 | 42 |
| 10 | Bicyclopyrone | 100 | 1000 | 3 | 5 |
| 12 |  | 400 | 1000 | 25 | 30 |
| 13 | Isoxaflutole | 100 | n/a | 13 | 10 |
| 15 |  | 400 |  | 30 | 23 |
| 16 | Isoxaflutole | 100 | 1000 | 15 | 3 |
| 18 |  | 400 | 1000 | 15 | 8 |
| 19 | Tembotrione | 100 | n/a | 23 | 17 |
| 21 |  | 400 |  | 25 | 20 |
| 22 | Tembotrione | 100 | 1000 | 3 | 0 |
| 24 |  | 400 | 1000 | 5 | 10 |
| 25 | Pyrasulfatole | 100 | n/a | 10 | 4 |
| 27 |  | 400 |  | 4 | 12 |
| 28 | Pyrasulfatole | 100 | 1000 | 10 | 0 |
| 30 |  | 400 | 1000 | 18 | 2 |
| 31 | Topramazone | 50 | n/a | 8 | 5 |
| 33 |  | 200 |  | 23 | 17 |
| 34 | Topramazone | 50 | 1000 | 5 | 2 |
| 36 |  | 200 | 1000 | 0 | 3 |

These results demonstrate that iron chelates can be used to mitigate damage from the HPPD herbicides mesotrione, bicyclopyrone, isoxaflutole, tembotrione and pyrasulfatole when applied over the top of the HPPD-tolerant soybean events SYHT0H2 and SYHT04R.

Experiment 9

Effect of Iron Chelates in Mitigating Foliar Bleaching Injury from HPPD Inhibiting Herbicides Across Various Transgenic HPPD Tolerant Tobacco Events Over-expressing HPPD Genes from Different Origins This experiment is carried out to determine whether iron chelates can mitigate the bleaching injury from HPPD inhibiting herbicides across various transgenic HPPD tolerant tobacco events over-expressing HPPD genes from different origins. These experiments are conducted using three distinct HPPD-overexpressing *Nicotiana tabacum* cv *Samsun* (tobacco) lines, one over-expressing wheat HPPD, one overexpressing an *Avena* HPPD and one over-expressing a HPPD from a bacterial source, *Pseudomonas florescens*. For each transgenic line, five identical clonal plants were sprayed with each herbicide treatment. Two untransformed clonal tobacco plants are also sprayed (200l/ha) with each herbicide treatment. Assessments are carried out 3, 7 and 14 days after herbicide application.

The results obtained are summarised in the Table below. All scores represent average % herbicide damage. The results demonstrate significant safening is conferred by the inclusion of iron chelates in the herbicide applications. An equivalent safening effect is not observed when the same chemical treatments are applied to wild type plants. This study clearly indicates that the mitigating effect of water soluble iron containing compounds on HPPD inhibitor damage previously observed in soybean overexpressing HPPD is also apparent in other plant species overexpressing HPPD, such as tobacco. It further demonstrates that the effect is not specific to HPPD tolerance genes from a single source, but to HPPD tolerance genes derived from different plant and bacterial sources.

|  | Mesotrione | Sequestrene | 3DAA | | | | | | 7DAA | | | | | | 14DAA | | | | | | |
|---|---|---|---|---|---|---|---|---|---|---|---|---|---|---|---|---|---|---|---|---|---|
| Trt No. | (gai/ha) | 138 (g/ha) | *Pseudomonas* HPPD | | | | WT | | *Pseudomonas* HPPD | | | | WT | | *Pseudomonas* HPPD | | | | WT | | |
| 1 | 50 |  | 10 | 20 | 30 | 10 | 15 | 60 | 65 | 20 | 20 | 35 | 15 | 25 | 80 | 80 | 15 | 20 | 30 | 10 | 20 | 85 | 85 |
| 2 | 100 |  | 35 | 25 | 25 | 20 | 35 | 70 | 70 | 55 | 30 | 30 | 30 | 35 | 80 | 80 | 40 | 25 | 25 | 20 | 30 | 85 | 90 |
| 3 | 150 |  | 40 | 30 | 20 | 45 | 40 | 55 | 60 | 60 | 35 | 30 | 70 | 40 | 80 | 80 | 55 | 30 | 20 | 75 | 35 | 85 | 85 |
| 4 | 50 | 1000 | 5 | 5 | 10 | 10 | 20 | 50 | 50 | 0 | 0 | 0 | 0 | 0 | 80 | 80 | 0 | 0 | 0 | 0 | 0 | 70 | 75 |
| 5 | 100 | 1000 | 10 | 5 | 10 | 5 | 10 | 60 | 60 | 0 | 0 | 0 | 0 | 0 | 80 | 80 | 15 | 5 | 0 | 0 | 0 | 75 | 85 |
| 6 | 150 | 1000 | 5 | 5 | 15 | 10 | 15 | 60 | 60 | 5 | 15 | 15 | 0 | 0 | 80 | 80 | 5 | 5 | 5 | 0 | 0 | 85 | 85 |

|  | Mesotrione | Sequestrene | 3DAA | | | | 7DAA | | | | 14DAA | | | |
|---|---|---|---|---|---|---|---|---|---|---|---|---|---|---|
| Trt No. | (gai/ha) | 138 (g/ha) | Wheat HPPD | | WT | | Wheat HPPD | | WT | | Wheat HPPD | | WT | |
| 7 | 200 |  | 10 | 5 | 10 | 5 | 10 | 60 | 60 | 10 | 0 | 0 | 0 | 0 | 80 | 80 | 10 | 10 | 0 | 10 | 10 | 85 | 85 |
| 8 | 300 |  | 15 | 10 | 10 | 10 | 10 | 65 | 65 | 20 | 15 | 15 | 20 | 5 | 80 | 80 | 15 | 10 | 15 | 0 | 5 | 90 | 85 |

| Trt No. | Mesotrione (gai/ha) | Sequestrene 138 (g/ha) | 3DAA Avena HPPD | | | | | WT | | 7DAA Avena HPPD | | | | | WT | | 14DAA Avena HPPD | | | | | WT | |
|---|---|---|---|---|---|---|---|---|---|---|---|---|---|---|---|---|---|---|---|---|---|---|---|
| 9 | 400 | | 20 | 20 | 15 | 20 | 20 | 55 | 60 | 20 | 25 | 20 | 20 | 20 | 80 | 80 | 20 | 25 | 15 | 15 | 10 | 85 | 85 |
| 10 | 200 | 1000 | 0 | 0 | 0 | 0 | 5 | 55 | 60 | 0 | 0 | 0 | 0 | 0 | 80 | 80 | 20 | 5 | 15 | 10 | 0 | 85 | 85 |
| 11 | 300 | 1000 | 0 | 5 | 5 | 10 | 0 | 50 | 60 | 10 | 5 | 0 | 0 | 0 | 80 | 80 | 10 | 5 | 15 | 10 | 0 | 90 | 85 |
| 12 | 400 | 1000 | 10 | 0 | 0 | 0 | 10 | 55 | 60 | 5 | 0 | 0 | 0 | 0 | 80 | 80 | 10 | 10 | 5 | 5 | 5 | 90 | 85 |
| 13 | 400 | | 55 | 45 | 50 | 60 | 40 | 50 | 55 | 70 | 65 | 65 | 70 | 65 | 80 | 80 | 65 | 45 | 45 | 65 | 50 | 95 | 90 |
| 14 | 500 | | 55 | 60 | 65 | 65 | 65 | 55 | 60 | 75 | 70 | 75 | 75 | 75 | 80 | 80 | 70 | 65 | 70 | 65 | 60 | 85 | 85 |
| 15 | 600 | | 30 | 65 | 60 | 40 | 60 | 55 | 55 | 55 | 75 | 75 | 55 | 78 | 80 | 80 | 40 | 65 | 65 | 50 | 70 | 85 | 85 |
| 16 | 400 | 1000 | 0 | 5 | 0 | 10 | 0 | 60 | 55 | 15 | 15 | 10 | 10 | 0 | 80 | 80 | 15 | 10 | 5 | 5 | 15 | 90 | 95 |
| 17 | 500 | 1000 | 15 | 5 | 50 | 40 | 55 | 50 | 60 | 15 | 0 | 50 | 40 | 65 | 80 | 80 | 15 | 5 | 40 | 35 | 60 | 90 | 90 |
| 18 | 600 | 1000 | 55 | 50 | 55 | 35 | 25 | 55 | 55 | 65 | 65 | 65 | 40 | 30 | 80 | 80 | 60 | 65 | 55 | 35 | 15 | 90 | 85 |

The invention claimed is:

1. A method of improving the tolerance of a plant, which has been genetically engineered to over express a p-hydroxyphenylpyruvate dioxygenase (HPPD), to a HPPD inhibiting herbicide, said method comprising applying to said plant a water-soluble iron-containing compound comprising an iron chelate wherein the chelate is selected from the group consisting of ethylenediamine tetraacetic acid (EDTA), 2-[2- [[2-Hydroxy- 1 -(2-hydroxyphenyl)-2-oxoethyl]amino]ethylamino]-2-(2-hydroxyphenyl)acetic acid (EDDHA) and diethylenetriaminepentacetic acid (DTPA).

2. A method of selectively controlling weeds at a locus, the locus comprising weeds and crop plants, the crop plants having been genetically engineered to overexpress a HPPD which confers tolerance to a HPPD-inhibiting herbicide, the method comprising application to the locus of (i) a weed controlling amount of a HPPD-inhibiting herbicide and (ii) a water-soluble iron-containing compound comprising an iron chelate wherein the chelate is selected from the group consisting of ethylenediamine tetraacetic acid (EDTA), 2-[2- [[2-Hydroxy-1-(2-hydroxyphenyl)-2-oxoethyl]amino]ethylamino]-2-(2-hydroxyphenyl)acetic acid (EDDHA) and di ethylenetriaminepentacetic acid (DTPA).

3. The method according to claim 2, wherein the water-soluble iron-containing compound is applied to the crop plant simultaneously with the HPPD-inhibiting herbicide.

4. The method according to claim 1, wherein the plant is soybean.

5. The method according to claim 4, wherein the soybean contains a transgenic event selected from the group consisting of SYHT04R, SYHT0H2 and FG72.

6. The method according to claim 2, wherein the water-soluble iron-containing compound is a ferric sodium complex with EDDHA.

7. The method according to claim 2, wherein the water-soluble iron-containing compound is applied at a rate of from 100 to 4000 g/ha.

8. The method according to claim 2, wherein the HPPD-inhibiting herbicide is selected from the group consisting of mesotrione, bicyclopyrone, tembotrione and isoxaflutole.

* * * * *